United States Patent [19]
Nordström

[11] Patent Number: 5,895,413
[45] Date of Patent: Apr. 20, 1999

[54] SURGICAL SUTURE

[76] Inventor: Rolf E. A. Nordström, Annankatu 11 B 11, FIN-00120 Helsinki, Finland

[21] Appl. No.: 08/806,127

[22] Filed: Feb. 11, 1997

[30] Foreign Application Priority Data

Mar. 1, 1996 [FI] Finland ................................ 960968

[51] Int. Cl.$^6$ ........................................................ A61B 17/04
[52] U.S. Cl. ......................................... 606/228; 606/231
[58] Field of Search .................................... 606/228–231

[56] References Cited

U.S. PATENT DOCUMENTS

| | | | |
|---|---|---|---|
| 3,454,011 | 7/1969 | Wagner | 128/335.5 |
| 4,905,367 | 3/1990 | Pinchuk et al. | 29/458 |
| 5,147,382 | 9/1992 | Gertzman et al. | 606/228 |
| 5,263,971 | 11/1993 | Hirshowitz et al. | 606/216 |

FOREIGN PATENT DOCUMENTS

| | | | |
|---|---|---|---|
| WO 93/21849 | 11/1993 | WIPO | A61B 19/00 |
| WO 94/26173 | 11/1994 | WIPO | A61B 17/08 |

Primary Examiner—Gary Jackson
Attorney, Agent, or Firm—Baker & Maxham

[57] ABSTRACT

The invention relates to a surgical suture which can be used for stitching together extensive skin deformations or skin areas desired to be surgically removed or in view of preventing the expansion of the scar of conventional surgical wounds. Therefore, the suture of the invention is made of silicone elastomer having a visco-elastic elongation of more than 50%, preferably more than 100% and an elongating force of only 1–20N when the elongation is 100%.

9 Claims, 1 Drawing Sheet

SURGICAL SUTURE

BACKGROUND OF THE INVENTION

The present invention relates to a surgical suture which can be used for stitching up even extensive skin areas or skin deformations to be surgically removed or which can be used for precluding the expansion of the scar of conventional surgical wounds.

It is prior known that extensive deformations of skin areas can be surgically removed and the resulting tissue-devoid area can be closed by means of mechanical devices, described e.g. in Patent publications U.S. Pat. No. 5,263,971, EP-648093 and WO 93/21849, as well as by means of tissue expanders. The question is about the removal of skin deformations or the removal of a bald scalp area. However, the above-mentioned devices are expensive and inconvenient to use.

On the other hand, a problem with conventional surgical wounds is the expansion of scar in several portions of the body as the suture migrates in a certain manner within tissues gradually therethrough and the tissue extends and the scar may expand.

Patent publication U.S. Pat. No. 5,147,382 discloses a surgical suture having a useful yield elongation within the range of 2–9% and a visco-elastic elongation of 10–30% as well as a break elongation of 20–45%. The curves shown in FIGS. 1 and 2 of the publication indicate that the discussed filament has a stiffness which, even within the range of elastic elongation, is at least one order in excess of that of the present invention. A curve C depicted in FIG. 2 of the application corresponds more or less to this prior known case.

Even though the publication discloses the use of silicone elastomer as one of several alternatives the suture is excessively stiff to be used in the purpose of the invention for stitching together extensive removable skin areas or, in terms of conventional surgical wounds, for preventing the expansion of a scar for the reason that the suture or filament migrates through the tissue.

SUMMARY AND OBJECTS OF THE INVENTION

An object of the invention is to provide a surgical suture which, on the one hand, is suitable for stitching together extensive sections of skin to be removed and, on the other hand and in terms of conventional surgical wounds, is capable of preventing the expansion of a scar.

This object will be achieved by means of a surgical suture of the invention on the basis of the characterizing features set forth in the annexed claim 1. The non-independent claims disclose preferred embodiments for the invention.

BRIEF DESCRIPTION OF THE DRAWING

The invention will now be described in more detail with reference made to the accompanying drawings, in which.

DESCRIPTION OF THE PREFERRED EMBODIMENTS

Figure 1:
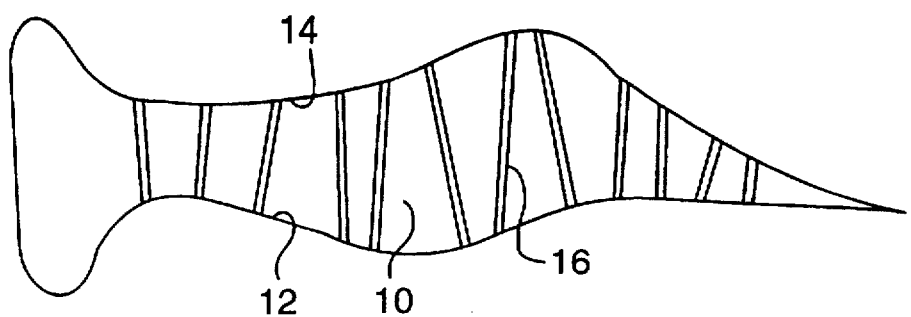
FIG. 1 shows an extensive skin-area wound which is stitched together by means of a suture of the invention and FIG. 2 illustrates stress-strain curves A and B for a suture of the present invention in comparison with a stress-strain curve C for conventional surgical sutures.
Figure 2:
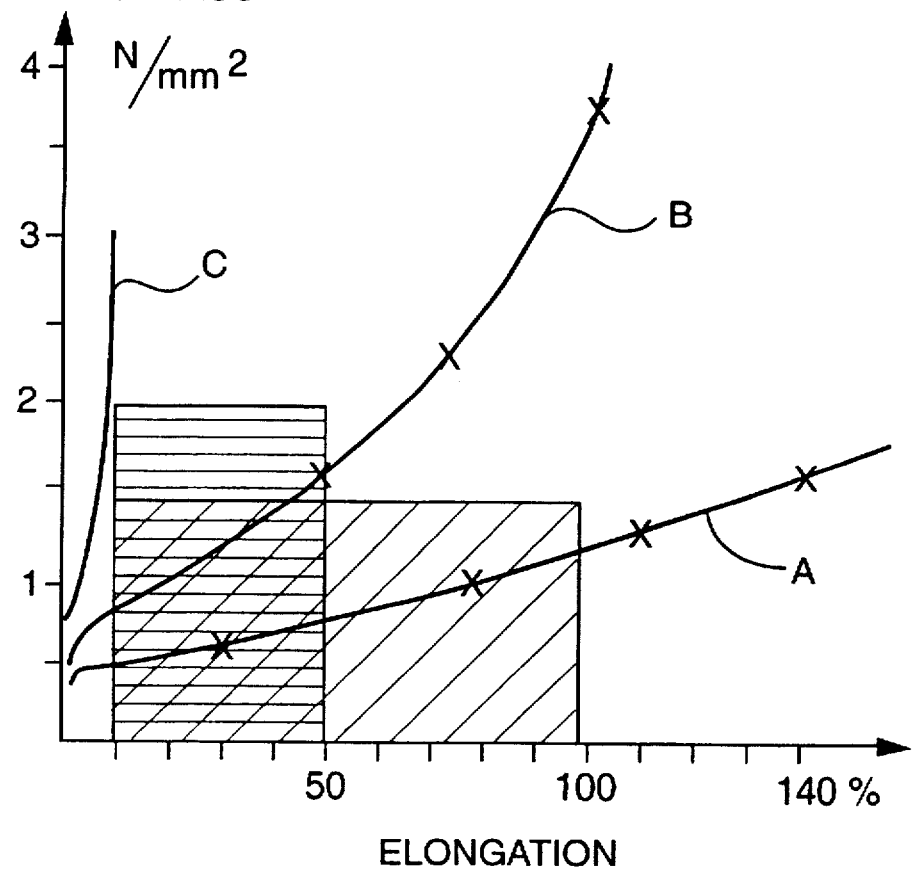

Referring to FIG. 1, a skin area wound 10 bordered by skin edges 12 and 14 is sutured together by means of suture 16 secured in a known manner by piercing the skin adjacent edges 12 and 14.

The suture material used for stitching a surgical wound is silicone elastomer. This type of suture or filament has a break elongation in excess of 500%, typically in excess of 700% and the filament has a breaking strength in excess of 500 N/cm$^2$, typically in excess of 800 N/cm$^2$. In view of an object of the invention, the filament diameter or thickness varies within the range of 0.5–3 mm. The filament cross-section may be circular, polygonal or flat.

The suture or filament stitched onto a wound may have an elongation which varies within the range of 0–100%. If the intention is to close extensive skin-area wounds, as in FIG. 1, the elongation is first typically within the range of 30–50% but, if necessary, may be more than that. Thus, as the edges of a wound draw closer to each other, the suture retains a wound closing force. When the suture is used in conventional surgical wounds, which do not involve the removal of extensive skin areas, the suture or filament may have a lower elongation but, even then, the continuing tensile stress of the filament prevents expansion of the scar.

The steepness of a stress-strain curve can be affected by adjusting the stiffness of elastomer by varying the mixing proportions of components and the number of catalysts or inhibitors. Depending on the stiffness of a filament material and the thickness of a filament, the filament or suture elongates 100% when the force is within the range of 1–20 N. This range of elongation and force can be used for handling wounds of varying sizes and in various types of tissue.

A suture of the invention offers a higher efficiency and a wider range of application than the prior known devices for stitching together extensive skin-area wounds. In addition, the suture of the invention is substantially more inexpensive. The types of silicone suitable for manufacturing the suture have been commercially available for a long time from various manufacturers. Monofilament sutures of a desired thickness are obtained by extruding silicone paste, prior to its final polymerization, through orifices of a suitable size.

I claim:

1. A surgical suture used for stitching a surgical wound in such a manner that the suture pierces a tissue at the edge of a wound, characterized in that the suture made of silicone elastomer has thickness within the range of 0.5 to 3 mm, has a visco-elastic elongation of from about 50% to greater than 100% and the elongating force is within the range of 1–20N when the elongation is 100%.

2. A surgical suture as set forth in claim 1, characterized in that the suture has a break elongation from about 500% to about 700%.

3. A surgical suture as set forth in claim 1, characterized in that the suture has a breaking strength from about 500N/cm$^2$ to about 800N/cm$^2$.

4. The surgical suture as set forth in claim 1, characterized in that over a range of application of the suture, wherein the suture stitched onto a wound has an elongation of 5–100%, the suture has a stress-strain curve which is nearly linear such that, as the edges of a wound draw closer to each other, the suture retains a wound closing force.

5. The surgical suture as set forth in claim 4, characterized in that the suture has a break elongation from about 500% to about 700%.

6. The surgical suture as set forth in claim 4 characterized in that the suture has a break elongation from about 500% to about 800N/cm$^2$.

7. The surgical suture as set forth in claim 4, characterized in that the suture has a breaking strength from about 500N/cm$^2$ to about 800N/cm$^2$.

8. The surgical suture as set forth in claim 4, characterized in that the suture has a breaking strength in excess of 800N/cm$^2$.

9. The surgical suture as set forth in claim 1, characterized in that the suture has a breaking strength in excess of 800N/cm$^2$.

* * * * *